United States Patent [19]
Goldberg et al.

[11] 3,951,135
[45] Apr. 20, 1976

[54] COMPRESSED DATA DISPLAY SYSTEM

[75] Inventors: Herbert Emanuel Goldberg, Concord; Robert Lee Cannon, Waltham; David L. Smith, Bedford, all of Mass.

[73] Assignee: American Optical Corporation, Southbridge, Mass.

[22] Filed: Apr. 4, 1975

[21] Appl. No.: 565,306

Related U.S. Application Data

[62] Division of Ser. No. 441,684, Feb. 11, 1974, Pat. No. 3,893,453.

[52] U.S. Cl. .................. 128/2.06 G; 346/33 ME
[51] Int. Cl.² ............................................ A61B 5/04
[58] Field of Search ............... 128/2.05 Q, 2.05 R, 128/2.06 A, 2.06 B, 2.06 F, 2.06 G, 2.06 R, 2.06 V; 346/33 ME, 63, 68, 79, 101, 103, 112, 138

[56] References Cited
UNITED STATES PATENTS

| | | | |
|---|---|---|---|
| 2,235,894 | 3/1941 | Lee | 128/2.05 R |
| 2,539,009 | 1/1951 | Chaney et al. | 346/138 |
| 2,635,195 | 4/1953 | Hancock | 128/2.06 G |
| 2,718,224 | 9/1955 | Apstein | 128/2.06 G |
| 2,741,530 | 4/1956 | Hill | 346/138 |
| 3,302,639 | 2/1967 | Koffler | 128/2.06 G |
| 3,478,364 | 11/1969 | Frank | 128/2.06 B |
| 3,681,774 | 8/1972 | Harris et al. | 128/2.06 G |

*Primary Examiner*—William E. Kamm
*Attorney, Agent, or Firm*—H. R. Berkenstock, Jr.; William C. Nealon

[57] ABSTRACT

A compressed data display system. There is disclosed a system for recording over extended periods of time EKG and other vital signs of a patient and for automatically displaying the waveforms in a compressed and readily interpretable manner. The EKG waveform is recorded on looped paper supported by and/or wrapped around rotatable drum or drums which may have cylindrical shape. The EKG is recorded in helical or spiral fashion by simultaneously rotating the drum and transversely moving a galvanometer pen in the direction of the axis of rotation of the drum or cylinder. After the paper is removed, if it is a continuous or closed loop, it can be slit and opened into a single sheet. The recorded EKG waveforms are thus displayed compressed in a line-over-line manner and provide the physician with a clear picture of the patient's heart activity for extended periods of time.

17 Claims, 5 Drawing Figures

COMPRESSED DATA DISPLAY SYSTEM

This is a division of application Ser. No. 441,684, filed Feb. 11, 1974, which has matured into U.S. Pat. No. 3,893,453.

BACKGROUND OF THE INVENTION

1. Field of the Invention

The present invention relates generally to the field of medical electronics. More specifically, the present invention relates to means for monitoring and displaying vital signs including EKG of a patient in a line-over-line compressed-data manner which facilitates analysis.

2. Description of Prior Art

Over the years, various medical-electronic systems have been developed which aid physicians in diagnosing and providing therapy to patients. Particularly, in the area of cardiology and heart disease, there have been significant advances. For example, heart pacers and EKG monitoring equipment are but two of the types of equipment that have proved to be valuable to physician and patient alike. These devices are now tending to become somewhat familiar to laymen as well.

As is well known in the medical field, EKG strips are taken by a physician by attaching leads or conductors to the body of a patient (generally three leads). Electrical signal activity generated by the patient's heart is sensed by these conductors or sensors. These electrical signals are extended to EKG amplifiers and eventually to galvanometer pens for scribing on the surface of a paper. The paper is generally spool-wound chart paper and advanced in a continuous manner, the direction of advance of paper being the direction of a time axis. Deflections of the galvanometer pen are generally perpendicular or transverse to direction of motion of the paper. The resultant trace, if the EKG is taken for any appreciable length of time, is very long. Anyone with experience in this field knows that the accumulated chart paper is unwieldy and cumbersome. It is thus difficult to accurately compare a patient's heart activity over periods of an hour or more when the EKG is left running continuously. Simply, too much paper exists for facile manual control and analysis. This is a severe problem of the prior art.

The present invention is a solution to the prior art problem of recording and displaying large quantities of vital sign data and particularly the EKG of a patient. It provides an automatic line-over-line compression of data in a compact and easily usable form and thus facilitates analysis.

SUMMARY OF THE INVENTION

The present invention relates to recording of vital sign data on a paper or chart paper wrapped around a cylindrical drum or drums. The galvanometer pen is translated in a direction transverse to direction of movement of the chart paper. The chart paper direction is one time axis, and the direction of motion of the galvanometer pen is a second quantized time axis. Continuous transverse motion of the galvanometer pen permits scribing a helix on the surface of the cylinder's chart paper. Deflections due to the EKG signal are in directions also transverse to direction of chart paper motion. The display system includes EKG sensing and amplifying means, a rotatably mounted cylinder, closed loop chart paper fitted to the cylinder, and a transversely movable galvanometer pen assembly for scribing on the paper in the manner described above. Another feature of the present invention includes circuitry for providing a dithering mark at selected portions of the recorded data either upon manual command or automatically to indicate the average rate of heartbeat for a given portion of EKG data.

An advantage of the present invention is that it compresses vital sign data, from a long paper trace readout into a single sheet line-over-line vital sign "picture" thereby facilitating analysis. It is thus advantageous to patient and physician alike.

It is thus an object of the present invention to provide an improved system for displaying vital signs of a patient.

It is another object of the present invention to provide an improved EKG monitor and display device.

It is a further object of the present invention to provide an improved EKG display system that has means for indicating average heartbeat rate for a selectable period of time and has means for marking occurrences of other events on a chart paper trace.

Other objects and advantages of the present invention will become apparent to one having reasonable skill in the art after referring to the detailed description of the appended drawings in which:

DESCRIPTION OF THE PREFERRED EMBODIMENTS

Figure 1:
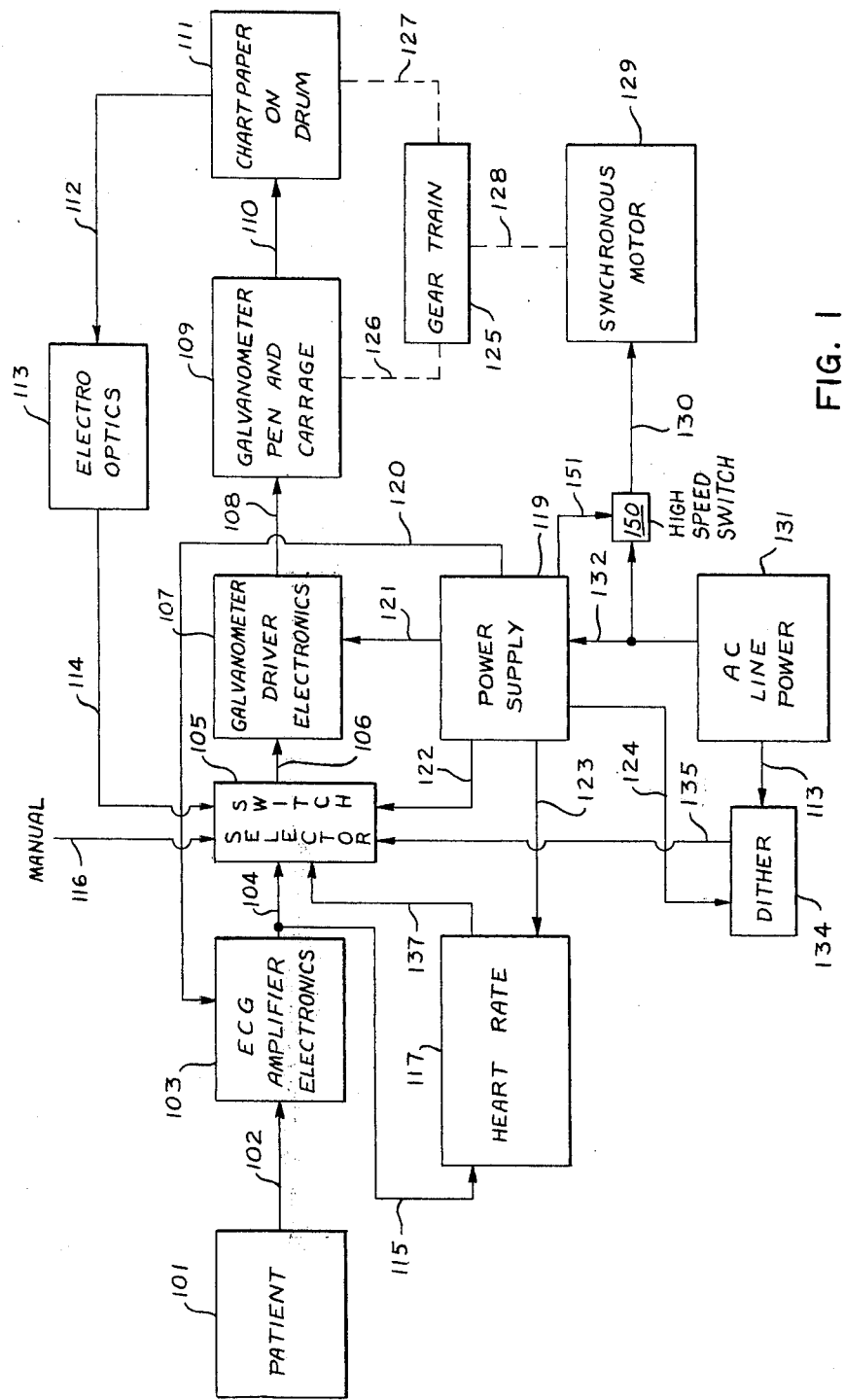
FIG. 1 depicts a block diagram of an illustrative embodiment of the present invention.

In FIG. 1, patient 101 is connected by EKG leads 102 to EKG (ECG) amplifier electronics 103. (Herein, a conductor or lead is intended to imply conductors or leads if appropriate.) Output from amplifier electronics 103 is extended on conductor 104 to selector switch 105. Likewise, output from ECG amplifier electronics 103 is extended on conductor 115 to heart rate module 117. Output from heart rate module 117 is extended to selector switch 105 on conductor 137. Output from selector switch 105 is provided on conductor 106 to galvanometer drive electronics 107. Output from electronics 107 is extended on conductor 108 to galvanometer pen and carriage assembly 109. Scribing output from carriage assembly 109 is provided to chart paper on drum 111 via input (pen) 110. This is the basic sensing, amplifying, monitoring, and recording (and/or displaying) functional chain.

Synchronous motor 129 provides rotational mechanical output 128 to gear train 125 which, in turn, provides rotational outputs 126 and 127 to assembly 109 and drum 111, respectively. Synchronous motor 129 is supplied by AC line power 131 through speed control 150 on conductor 130. AC line power 131 likewise provides power inputs to power supply 119 on conductor 132, and to dither circuitry 134 on conductor 133.

Power supply 119 is a DC power supply, and supplied DC voltage to dither circuitry 134 over conductor 124, heart rate module 117 over conductor 123, selector switch 105 over conductor 122, electronics 107 over conductor 121, amplifier electronics 103 over conductor 120, and speed control 150 over conductor 151.

A rotational position input 112 is provided from cylindrical drum 111 to electro-optics 113. The output from electro-optics 113 is provided to selector switch 105 on conductor 114. A manual input 116, in the form of a pushbutton switch (not shown) or other switch, is provided to selector switch 105.

Figure 2:
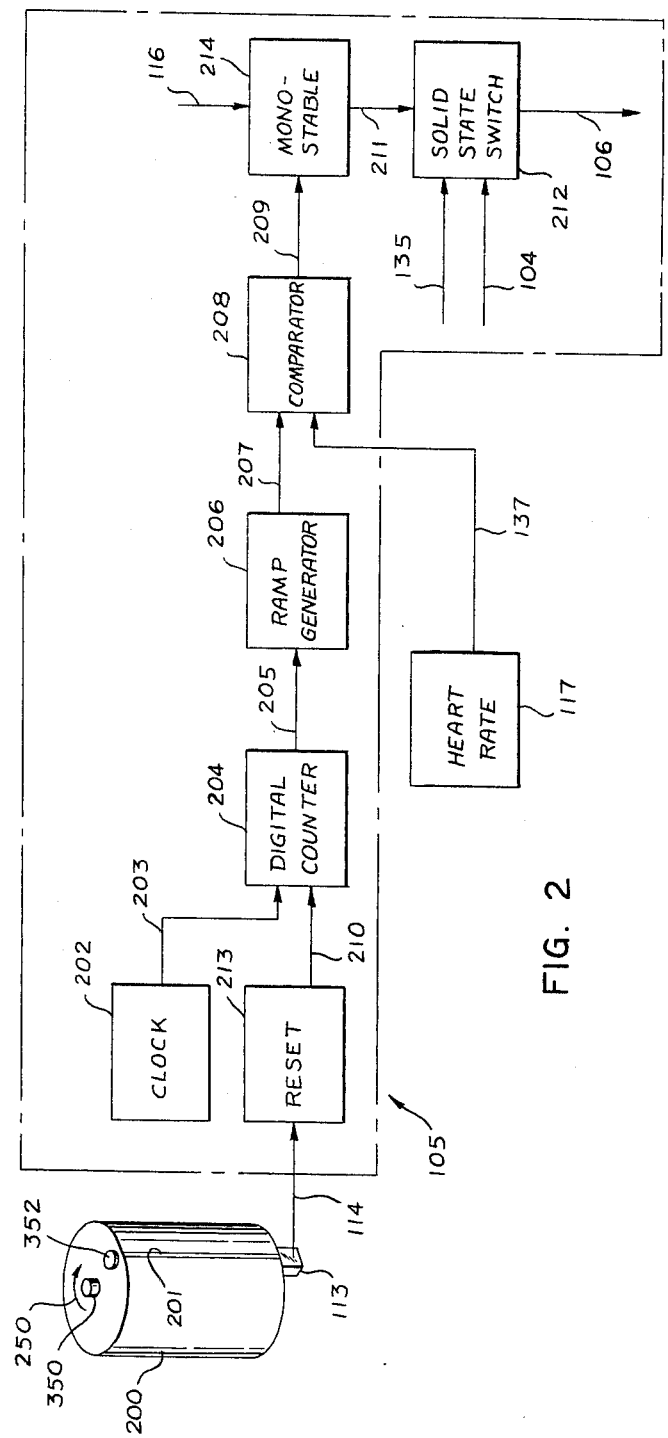
FIG. 2 depicts certain detail of the block diagram of FIG. 1.

Referring now to FIG. 2, cylindrical drum 200, which rotates in direction 250, shows axially directed slit 201 at its surface. Electro-optics assembly 113, located in general at the periphery of the cylinder, provides input 114 through selector switch 105. (In FIG. 2, phantom line 105 represents the outline of selector switch 105 as shown in FIG. 1.) Input 114 is provided to reset circuitry 213, output thereof being extended on conductor 210 to digital counter 204. The other input to counter 204 is provided on conductor 203 from clock 202. Counter 204 provides an output on conductor 205 to ramp generator 206. Output from ramp generator 206 is extended on conductor 207 to one input of comparator 208. The other input of comparator 208 is provided by heart rate module 117 on conductor 137. Output from comparator 208 is extended on conductor 209 as an input to mono-stable circuitry 214. Another input to mono-stable circuitry 214 is manual input 116. Output from mono-stable circuitry 214 is provided to solid state switch 212 on conductor 211. Other inputs to solid state switch 212 include inputs on conductors 135, and 104. Ouput from solid state switch 212 is extended on conductor 106 to galvanometer drive electronics 107 as indicated in FIG. 1.

Figure 3:
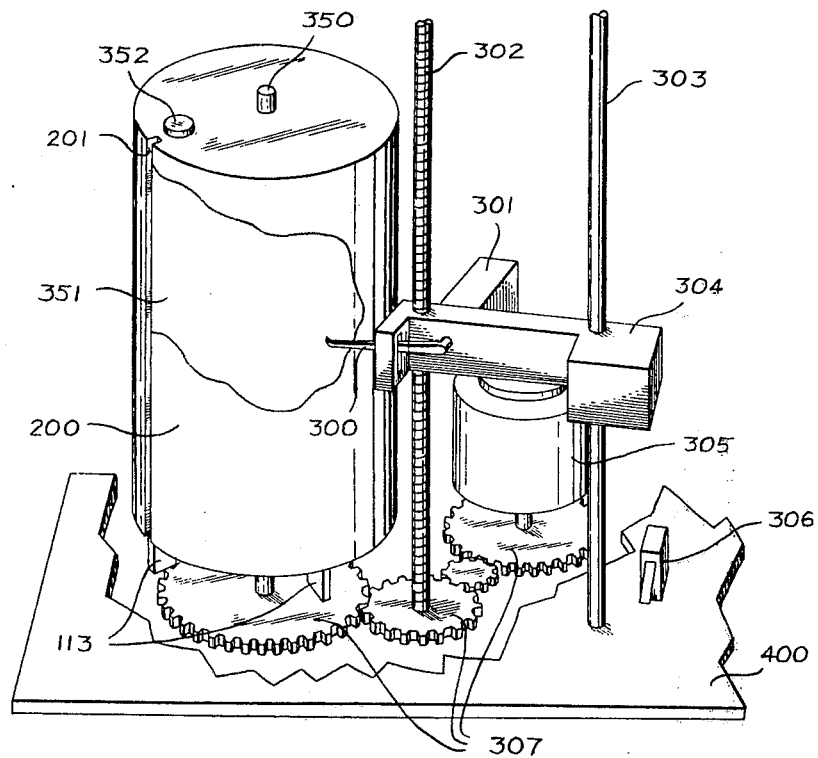
FIG. 3 depicts a perspective view of certain mechanical detail of the illustrative embodiment of the present invention.
Figure 4:
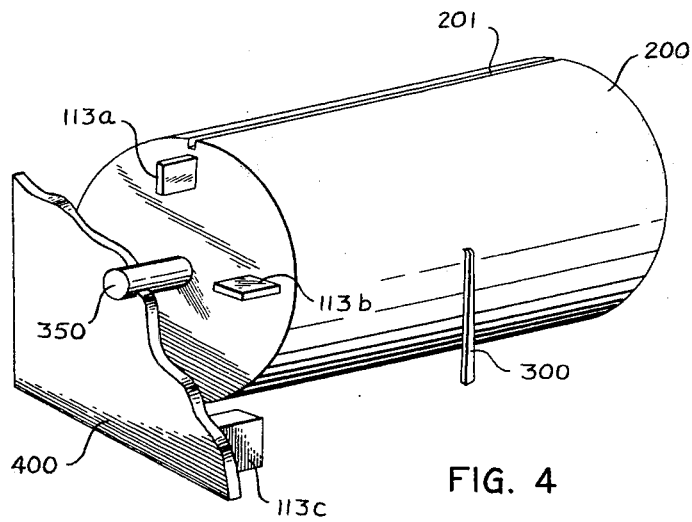
FIG. 4 depicts another perspective view of other certain mechanical aspects of the illustrative embodiment of the present invention.

Next, proceeding with description of FIGS. 3 and 4 prior to describing operation of the preferred embodiment, FIG. 3 depicts cylinder or writing surface 200 with slit 201, the writing surface rotatably mounted about a substantially vertical axis 350. Writing surface 200 can have cylindrical, conical, or other shape. Writing surface 200 is intended to be adapted for magnetic drum recording as well as paper displays. This axis need not be vertical; however, for purposes of clarity of illustration it is herein thus depicted. Axis 350 is shown rotatably mounted to base or chassis 400 in FIG. 4. Galvanometer pen 300 is arranged to scribe on the surface of cylinder or drum 200, there being chartpaper or paper 351 (partially indicated for purposes of clarity of illustration) wrapped around and fastened in slit 201. It is to be understood that paper 351 extends the entire substantial length of cylinder or drum 200 and essentially wraps around and covers the surface area of the drum. Pen 300 scribes or writes on paper 351.

Lead screw 302 is shown substantially parallel to axis 350 and is likewise rotatably mounted to chassis 400. Rod 303 is fixedly mounted parallel to lead screw 302. Sliding on rod 303 is slidably mounted carriage 304 which, in turn, supports galvanometer 301. Galvanometer 301 receives an electrical signal input on conductor wires (not shown in FIGS. 3, 4) which signals are transduced into mechanical motion of pen 300. Motor 305 (depicted in FIG. 1 as 129) provides rotational output to gear train 307 (depicted in FIG. 1 as 125). The gear train provides rotational motion 250 to cylinder 200 about axis 350, and provides rotational motion to lead screw 302 about its longitudinal axis. Carriage 304 is threadingly engaged with threads of lead screw 302. Thus, rotational motion of lead screw 302 provides translational motion of carriage 304 in a direction substantially parallel to axis 350. Gears of gear train 307 are designed to provide a plurality of rotations of drum 200 corresponding to a single motion in a translational manner from the top of drum 350 (an initial position) to the bottom of drum 350 (a final position). Thus, gear train 307 need not have the specific arrangement depicted in FIG. 3. When chassis 304 reaches final position, it makes physical contact and operates micro-switch 306. The micro-switch is electrically connected between power 131 and motor 305, and operation of the microswitch disconnects power to the motor thereby stopping the rotational and translational motions of the system. There is provided carriage disengagement means (Not shown) for rapid return of the galvanometer to the initial position, not causing the drum to rotate.

In FIG. 1, electro-optics 113 was depicted as being functionally connected between the drum and the selector switch 105. In FIGS. 3 and 4, the electro-optics, which is comprised of phototransistors and photodiodes, commercially available, are mounted as shown. Electro-optic elements 113a and 113b are approximately 90° displaced on the periphery of one end of drum 200. These electro-optical elements rotate with the rotating drum. Mounted on base or chassis 400 is a fixed electro-optic sensor 113c. As the rotatable electro-optical elements 113a and 113b in turn pass adjacent electro-optical element 113c, optical communication is achieved there between. The purposes of these optical elements will be discussed more fully below.

Slit 201 is shown in FIGS. 2, 3, and 4. Chart paper having fixed length and having substantially parallel edges may be wrapped around drum 200. Edges of paper 351 are inserted into slit 201 and are fastened therein by rotatable clamping control 352.

Figure 5:
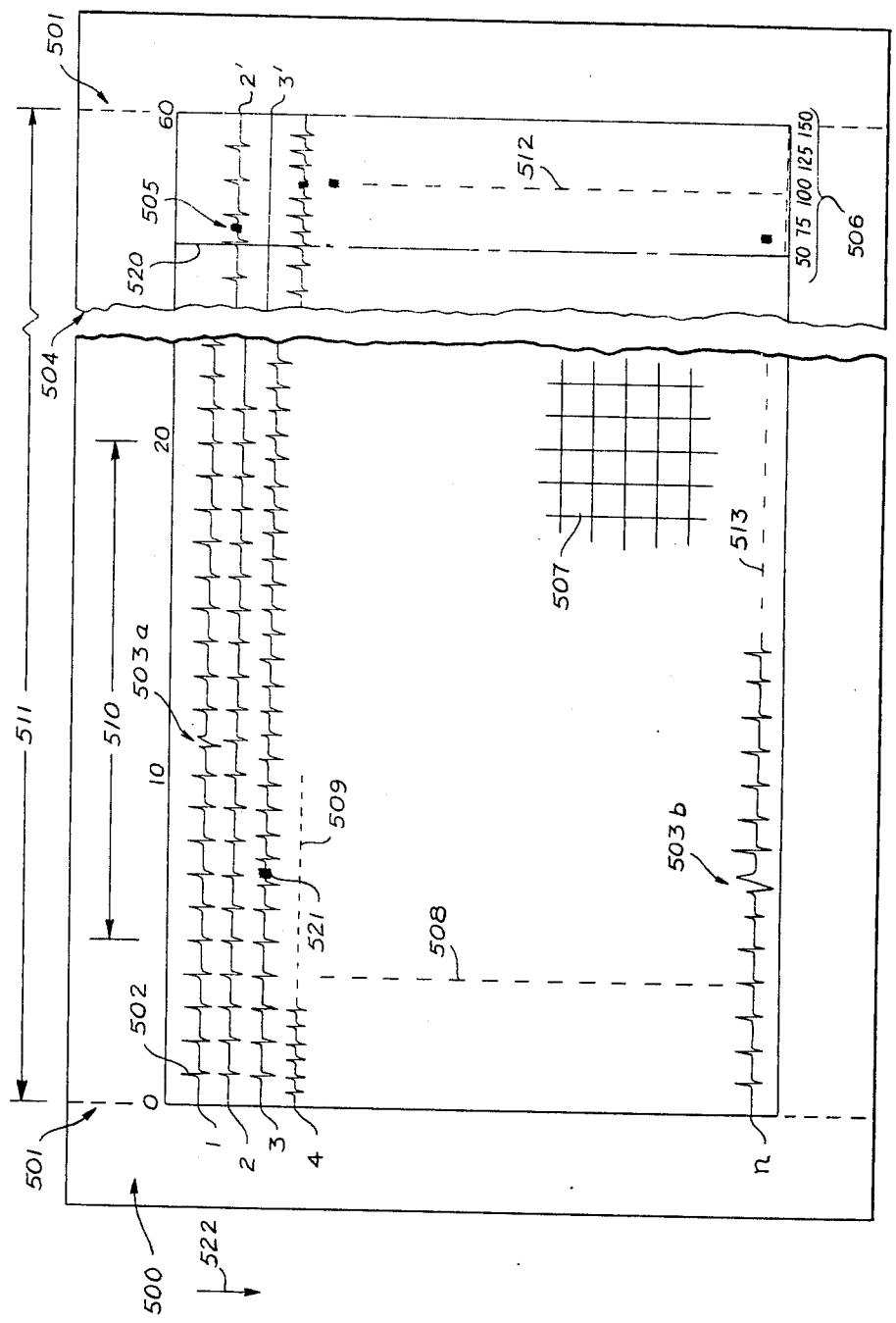
FIG. 5 depicts the resultant chart paper compressed data display generated by the present invention.

In operation, the preferred embodiment as described in FIGS. 1-4, and the obtained display of FIG. 5 to be described, provides a compressed EKG (or other vital sign) data display. The EKG signal of patient 101 is amplified in electronics 103, extended to selector switch 105, extended to galvanometer driver electronics 107 which drives galvanometer pen means 301 which in turn causes pen 300 to scribe on paper 351 supported on cylinder 200. While this signal is being applied to pen 300 and while scribing motion is taking place, cylinder or drum 200 rotates in direction 250. Simultaneously carriage 304 translated in a downward vertical direction. This combined rotational and translational motion creates a helical base line on paper 351. (It is intended herein that the words "helix", "spiral" and "coil" can be used interchangeably.) The result can be seen in FIG. 5.

In FIG. 5, paper 500 (which is shown partially as paper 351 in FIG. 3) is depicted as having usable display length 511 which corresponds to the circumference of drum 200. Dotted lines 501 indicate where folds of the paper are made for insertion of these folds into slit 201 as described earlier. Paper 500 is shown in a broken diagrammatic fashion for purposes of clarity of illustration. A time scale of zero through 60 seconds is provided and break 504 in the paper takes place at approximately between 23 seconds and 53 seconds.

The scribing of pen 300 on paper 500 provides EKG wave forms 502. As intended to be depicted by lines 508, 509, 512, and 513, the entire surface of the page can be scribed with EKG signals. As noted earlier, the base line scribed on the surface of paper 500 when mounted on drum 200 would be a helix or spiral. When the paper is removed from slit 201 and opened flat, straight lines with a slightly downward slope are observed. Thus, data line 2 identified by numeral 2 at the left-hand edge of the useable display paper, corresponds in time to the end of data line 1 identified as 2' at the right-hand data edge of the paper.

In other words, lines of EKG data are identified by numerals 1, 2, 3, and 4 . . . .n, and the end of each line corresponds in time to the beginning of the next successive line. Thus, the point marked 2' corresponds in time to the end of line 1 and the beginning of line 2. The designation n indicates that there are an extensive plurality of data lines obtained and limited only by size of paper and drum. The preferred embodiments are designed to provide 60 seconds of data per line with 30 lines per sheet thereby displaying ½ hour of electrical heart activity and to provide 4 minutes per line with 30 lines per sheet thus providing a 2 hour display.

Reference numeral 510 depicts a selectable period of time during which heart rate is averaged in heart rate module 117 comprised of standard circuitry. Module 117 is triggered by each EKG wave to provide a constant width and constant amplitude pulse output in response thereto. This pulse train is then averaged on capacitor circuitry or other means to provide a DC level corresponding to average heart rate.

Turning to FIG. 2, heart rate module 117 provides this DC voltage to comparator 208. Digital counter 204 is reset by a signal coming from optics 113 when pen 300 is positioned at slit 201 as will be fully explained below. This is the zero or reset setting for the scribing motion. Digital counter 204 is stepped by clock generator 202 once each second. Clock generator 202 is synced to 60 hertz power 131. At a predetermined count, which according to FIG. 5 is equal to about 56 counts (or 56 seconds), ramp generator 206 is energized. Counter 204 is constructed from standard digital circuitry and may be a ring counter. Ramp generator 206 is likewise constructed from standard circuitry for charging a capacitor in a linear fashion. Thus, ramp generator 206 is energized after about 56 seconds and this energization takes place at line 520 on FIG. 5. Comparator 208 compares the two inputs and at coincidence between ramp generator voltage and DC voltage on conductor 137, the comparator output is extended on conductor 209 to monostable 214. Comparator 208 is likewise standard operational amplifier circuitry. Omission of detailed discussion of the circuit elements in these standard circuits does not inhibit full understanding of the present invention.

In FIG. 1, dither generator 134 is powered by AC line power 131 and is a conduit for 60 hertz power at a substantially reduced power value. This 60 cycle/second signal is provided on conductor 135 in FIG. 2, to solid state switch 212. Operation of monostable 214 causes connection of the dithering signal on conductor 135 to output conductor 106. Solid state switch 212 is comprised of standard transistor switching circuitry and omission of detailed description does not detract from complete understanding of the present invention. The average DC voltage generated by heart rate module 117 corresponds to rate scale 506 in FIG. 5 and thus, dithering mark 505 is indicated to be approximately 60 beats per minute. After a predetermined period of time determined by time constants of monostable 214, solid state switch 212 returns to its prior connection of conductors 104 and 106, thereby reconnecting the EKG signal to pen 300. Mark 505 indicates average heartbeat rate for time period 510 of line 1. Accordingly, a dithering rate mark is provided in the other lines of data. This is very useful information since it provides at a glance a histogram effect of heartbeat rate change of the patient over a long period of time.

Numeral 503a and 503b refer to ectopic beats, which are clearly visible in this display. Another module which detects ventricular premature beats (a form of ectopic beats) can be connected between conductor 115 and selector switch 105 in a manner similar to connection of module 117. A premature ventricular contraction detector is disclosed in U.S. Pat. No. 3,616,790 entitled MULTIFORM VENTRICULAR PREMATURE BEAT DETECTOR issued on Nov. 2, 1971 in the name of G. J. Harris and assigned to Americal Optical Corporation, the Assignee of the present invention. Background information disclosed in this patent is incorporated herein by reference. Portions of circuitry disclosed in this patent can be used with other circuitry to provide a DC voltage corresponding to the number of PVC's per data line. Similarly to the histogram display of average heartbeat rate for a patient on a line by line basis, a separate histogram can be displayed at a different location on the paper having a different scale for indicating the number of occurrences of premature ventricular beats.

In FIG. 5, direction 522 represents direction of translational motion of carriage 304. Numerical designation 507 represents cross hatching which may be spread throughout the page in a uniform manner as depicted. It is illustrated only in a portion of sheet 500 for the purpose of clarity of illustration.

FIG. 1 and FIG. 2 indicate manual input 116 to selector switch 105 and more specifically to monostable circuitry 214. This utilizes a push-button or other manual switch arrangement whereby the physician or operator of the system can mark at will on sheet 500, a dither signal such as mark 521. As before, output 211 from monostable 214 causes solid state switch to make a connection between conductors 135 and 106. Dither generator 134 provides a 60 cycle dithering signal to conductor 106 and thus to pen 300 which scribes in a dithering or vibrating manner on chart paper 500. Dither mark 521 is displayed at this point in FIG. 5 for a special reason. It marks the occurrence of a significant event such as patient complaints of discomfort, or infusion of a drug, or the beginning of exercise testing, etc.

After 1 minute and 21 seconds of EKG recording, the patient is subjected to exercise testing (not shown, but can be treadmill walking with EKG leads attached to the patient). A feature of the present invention is a speed-up switch 150 as shown in FIG. 1. This speed-up push-button switch, which is designated on the chassis of the preferred embodiments as "reset", increases the speed of the synchronous motor 129 thereby operating gear train 125 more rapidly. As depicted in FIG. 5, line 2, after 22 seconds of recorded data, the galvanometer pen is translated to position 3' in a time which is equal to or less than the time between the last heartbeat and the next heartbeat. At point 3', the speed control 150 is returned to its standard speed arrangement. A purpose of this feature is to provide the beginning of exercise testing at a beginning point of line 3 for purposes of clarity of presentation for later analysis. Speed control 150 is a device which changes current flow to motor 129 (305).

Likewise, as noted the same display method can be utilized with other tests such as drug testing. If the patient is given certain drugs for medical reasons, the speed control can be operated to "reset" the display, where the heartbeats begin from the left-hand side of the paper as described above.

From FIG. 5, it is seen that approximately 8 seconds elapse after exercise begins before a noticeable change in heart rate occurs. This time value may not be realistic but does not detract from understanding of the present invention. Manual means 116 may also be operated to create designation 521 indicating the beginning of the increased heart rate.

Optical pick-ups 113a, 113b, and 113c are utilized in the operation of speed control 150 as well as in other features of the present invention. Speed control 150 is made to return to its original state when optical pickup 113b is in optical communication with pick-up 113c. At this point, galvanometer pen 300 is positioned at slit 201. A signal from optical pick-up 113c causes the switch in speed control 150 to return to its original state.

The optical pick-ups function in at least two modes. The first mode was described above. When the "reset button" is depressed speed control 150 is operated and causes drum 200 to move rapidly until optical pick-up 113b is aligned with optical pick-up 113c, (thus causing pen 300 to line up with slit 201). In another feature, when a "load button" is depressed, speed control 150 again increases speed of motor 129, thereby increasing speeds of rotation and translation of the system components. But, when optical pick-up 113a is in optical communication with 113c, all motion of the system is stopped. Control 150 disconnects motor 129 from AC power line 131. This load button is depressed when it is desired to have the slit position to the front of the apparatus for easy access regarding loading and unloading of the paper. Depressing the "run" button reconnects power to the motor.

The invention may be embodied in yet other specific forms without departing from the spirit or essential characteristics thereof. For example, one can use three galvanometers with three galvanometer pens to monitor EKG leads 102. Leads 102 generally are three in number, and each of these leads may be thus monitored. Thereby, lines 1, 2, and 3 in FIG. 5 could be made to represent the outputs from three leads 102 from patient 101. However, pitch or relative speed of lead screw 302 must be altered to accommodate this feature. In order for this to work properly, the end of line 1 would have to correspond to the beginning of line 4, being sufficiently displaced downward so as to not create interference with other lines corresponding to the other two leads. Furthermore, other sensors may be used to sense other vital signs (eg: blood pressure) simultaneously with EKG. For another example, it is to be understood that speeds other than constant speeds can be utilized in the translational motion and rotational motions of the invention. Rather than providing continuous translational motion of carriage 304 transverse to direction of paper motion, one could provide ratchet means for stepping carriage 304 in transverse manner upon each completion of a revolution of drum 200.

It is to be understood that other means of paper attachment could be made. An assembly cartridge including drum and paper could be used where one cylinder with paper is removed and another cylinder with paper is installed (where the paper is not a single sheet but is an endless loop or belt of paper).

Furthermore, if cylinder 200 were held in a horizontal position (rather than vertical as shown for purposes of clarity of illustration only), a paper loop of the endless belt variety (not shown), can be used which has a circumference in excess of the circumference of drum 200. The system works well if the scribing point of contact between pen 300 and the surface of the paper 351 on drum 200 remains smooth. Accordingly, even more data can be recorded and displayed. And another cylinder (not shown) can be installed at a remote distance, to provide pulley support means for this extended circumference endless paper loop. However, these are alternative embodiments and the preferred embodiment is that which is shown in the Figures.

It is to be further understood that more than 60 seconds or less than 60 seconds per line can be recorded and that more than or less than 30 lines per page can be recorded.

A particularly advantageous utility of the present invention is in connection with the transcription of EKG cassette tape recorders. Presently, portable tape recorders exist which record a patient's EKG for long periods of time, 24 hours or more. Playback of 24 hours of EKG data at real time would take thus 24 hours. On ordinary EKG chart paper, this would amount to many feet of paper. But, to playback this portable tape recorder data in a transcribing manner utilizing the present invention, both the tape recorder and the present invention's speed control can be increased by a factor of 20 or more (with respect to real time). Thus, all of this data can be recorded on a large single sheet of paper in an hour or less. The tremendous advantage of being able to analyze 24 hours of EKG activity of a patient within an hour or less after receiving that data on tape from the patient is clear.

Thus, the present embodiments are to be considered in all respects as illustrative and not restrictive, the scope of the invention being indicated by the appended claims rather than by the foregoing description and all changes which come within the meaning and range of the equivalency of the claims are therefor intended to be embraced therein.

What is claimed is:

1. A system for displaying vital signs of a patient, said system comprising: means for sensing said vital signs and for providing analogous electrical signals, means for amplifying said electrical signals, a chassis, means axially-rotatably mounted to said chassis for providing a writing surface, looped paper fitted to and supported by said writing surface means, means supported by said chassis for rotating said writing surface means thereby advancing and re-cycling said paper, galvanometer pen means for scribing on said paper in scribing directions transverse to the direction of motion of said paper, means connected to said chassis for supporting said pen means and for translationally moving said pen means in one of said scribing directions from an initial position towards a final position, means for extending said signals to said galvanometers pen means, and wherein said writing surface means comprises a cylinder having axially directed slit means in the surface of said cylinder and extending the entire length of said cylinder for receiving two substantially parallel edges of said paper and for clamping said edges to create a smooth overlapping of said paper around said cylinder.

2. A system as recited in claim 1 and wherein said cylinder means further comprises two electro-optical devices mounted on the periphery of said cylinder, said two devices being relatively angularly displaced by approximately 90°, one of said two electro-optical devices being mounted adjacent said slit, and a third electro-optical device mounted on said chassis adjacent said periphery and in substantial alignment with the scribing point between said paper and said pen means and arranged to be in optical communication with each of said two electro-optical devices as each of said two electro-optical devices rotates adjacent said third electro-optical device.

3. A system as recited in claim 2 including means responsive to the optical communication between said third electro-optical device and said other of said two electro-optical devices for controlling speed of said rotating means when said other of said two electro-optical devices is adjacent said third electro-optical device.

4. A system as recited in claim 2 including means responsive to the optical communication between said third electro-optical device and said one of said two electro-optical devices for inhibiting operation of said rotating means and said translationally moving means when said one of said two electro-optical devices is adjacent said third electro-optical device.

5. A system as recited in claim 1 and wherein said cylinder means further comprises two switching devices mounted on the periphery of said cylinder, said two devices being relatively angularly displaced by approximately 90°, one of said two switching devices being mounted adjacent said slit, and a third switching device mounted on said chassis adjacent said periphery and in substantial alignment with the scribing point between said paper and said pen means and arranged to be in communication with each of said two switching devices as each of said two switching devices rotates adjacent said third switching device.

6. A system for displaying vital signs of a patient, said system comprising: means for sensing said vital signs and for providing analogous electrical signals, means for amplifying said electrical signals, a chassis, means axially-rotatably mounted to said chassis for providing a writing surface, looped paper fitted to and supported by said writing surface means, means supported by said chassis for rotating said writing surface means thereby advancing and re-cycling said paper, means for establishing a recording rotational speed range, means for controlling said rotating means to operate within said recording rotational speed range, galvanometer pen means for scribing on said paper in scribing directions transverse to the direction of motion of said paper, means for extending said signals to said galvanometer pen means, means connected to said chassis for supporting said pen means and for translationally moving said pen means in one of said scribing directions from an initial position towards a final position, means for establishing a recording translational speed range as a function of said recording rotational speed range to permit said pen means to scribe said looped paper with representations of said signals in a non-overlapping path, and means for controlling said supporting and translationally moving means to operate within said recording translational speed range, and wherein said writing surface means comprises a cylinder having axially directed slit means in the surface of said cylinder and extending the entire length of said cylinder for receiving two substantially parallel edges of said paper and for clamping said edges to create a smooth overlapping of said paper around said cylinder.

7. A system as recited in claim 6 and wherein said rotating means includes means to provide a plurality of rotations of said writing surface means to correspond to the translational motion distance of said pen means in moving from said initial position to said final position.

8. A system as recited in claim 7 and wherein said recording rotational speed range establishing means permits said representations of said signals to be scribed on said paper in a compressed manner.

9. A system as recited in claim 8 further including manually-activated speed-control means for causing said rotating means and said translationally moving means to operate outside of said recording rotational speed range and said recording translational speed range respectively.

10. A system as recited in claim 9 and wherein said vital signs are the electrocardiogram of said patent.

11. A system as recited in claim 10 where said paper includes a heartbeat rate scale, said system further comprising means for providing an average heartbeat rate of said patient for a selectable period of time, means for generating a pen dithering signal, and means for momentarily disabling said extending means for conducting said pen dithering signal to said galvanometer pen means when said pen is scribing on said paper at a point which corresponds on said heartbeat rate scale to said average heartbeat rate.

12. A system as recited in claim 11 further comprising means for generating pen means dithering signals, and manually operated means for momentarily disabling said extending means and for conducting said dithering signals to said pen means, whereby a dither mark is scribed on said paper at will.

13. A system for displaying vital signs of a patient, said system comprising: means for sensing said vital signs and for providing analogous electrical signals, means for amplifying said electrical signals, a chassis, means axially-rotatably mounted to said chassis for providing a writing surface, looped paper fitted to and supported by said writing surface means, means supported by said chassis for rotating said writing surface means thereby advancing and re-cycling said paper, means for establishing a recording rotational speed range, means for controlling said rotating means to operate within said recording rotational speed range, galvanometer pen means for scribing on said paper in scribing directions transverse to the direction of motion of said paper, means for extending said signals to said galvanometer pen means, means connected to said chassis for supporting said pen means and for translationally moving said pen means in one of said scribing directions from an initial position towards a final position, means for establishing a recording translational speed range as a function of said recording rotational speed range to permit said pen means to scribe said looped paper with representations of said signals in a non-overlapping path, and means for controlling said supporting and translationally moving means to operate within said recording translational speed range, further including manually-activated speed-control means for causing said rotating means and said translationally moving means to operate outside of said recording rotational speed range and said recording translational speed range respectively.

14. A system as recited in claim 13 and wherein said speed control means further comprises two electro-optical devices employed in the control of the operation of at least said rotating means and mounted on the periphery of said cylinder, said two devices being relatively angularly displaced by approximately 90°, one of said two electro-optical devices being mounted adjacent said slit, a third electro-optical device mounted on said chassis adjacent said periphery and in substantial alignment with the scribing point between said paper and said pen means, and means for controlling optical communication between each of said two electro-optical devices as each of said two electro-optical devices rotates adjacent said third electro-optical device.

15. A system as recited in claim 14 including means responsive to the optical communication between said third electro-optical device and said other of said two electro-optical devices for returning speed of said rotating means within said recording rotational speed range when said other of said two electro-optical devices is adjacent said third electro-optical device.

16. A system as recited in claim 14 including means responsive to the optical communication between said third electro-optical device and said one of said two electro-optical devices for inhibiting operation of said rotating means and said translationally moving means when said one of said two electro-optical devices is adjacent said third electro-optical device.

17. A system as recited in claim 13 and wherein said speed control means further comprises two switching devices mounted on the periphery of said cylinder, said two devices being relatively angularly displaced by approximately 90°, one of said two switching devices being mounted adjacent said slit, and a third switching device mounted on said chassis adjacent said periphery and in substantial alignment with the scribing point between said paper and said pen means and arranged to be in communication with each of said two switching devices as each of said two switching devices rotates adjacent said third switching device.

* * * * *